US006528439B1

(12) United States Patent
Stokes et al.

(10) Patent No.: US 6,528,439 B1
(45) Date of Patent: Mar. 4, 2003

(54) CRIMPED POLYMERIC FIBERS AND NONWOVEN WEBS MADE THEREFROM WITH IMPROVED RESILIENCY

(75) Inventors: Ty J. Stokes, Suwanee, GA (US); Ryan C. Frank, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/164,106

(22) Filed: Sep. 30, 1998

(51) Int. Cl.[7] .................................................. D04H 1/70
(52) U.S. Cl. ...................... 442/352; 442/353; 442/392; 428/369; 604/358; 264/477; 264/495
(58) Field of Search ....................... 428/369; 442/352, 442/353, 392; 604/358; 264/477, 495

(56) References Cited

U.S. PATENT DOCUMENTS

| 3,514,248 A | * | 5/1970 | Martin et al. |
| 3,872,349 A | | 3/1975 | Spero et al. |
| 3,911,318 A | | 10/1975 | Spero et al. |
| 3,983,039 A | | 9/1976 | Eastland |
| 4,042,850 A | | 8/1977 | Ury et al. |
| 4,208,587 A | | 6/1980 | Eastlund et al. |
| 4,269,581 A | | 5/1981 | Ury et al. |
| 4,313,969 A | | 2/1982 | Matthews et al. |
| 4,359,668 A | | 11/1982 | Ury |
| 4,485,332 A | | 11/1984 | Ury et al. |
| 4,507,587 A | | 3/1985 | Wood et al. |
| 4,551,378 A | | 11/1985 | Carey, Jr. |
| 4,853,164 A | * | 8/1989 | Kiang et al. .................. 264/22 |
| 5,505,900 A | * | 4/1996 | Suwanda et al. ........... 264/477 |

FOREIGN PATENT DOCUMENTS

| DE | 3243932 | 1/1973 |
| EP | 0395336 A2 | 10/1990 |
| EP | 0586924 A1 | 3/1994 |
| EP | 0685579 A2 | 12/1995 |
| GB | 1603638 | 11/1981 |

OTHER PUBLICATIONS

International Search Report, Mar. 13, 2000.
Database WPI, Section Ch, Week 198931, Derwent Publications Ltd, Jun. 27, 1989, Abstract.
Patent Abstracts of Japan, vol. 013, No. 339, Jul. 31, 1989, & JP 01 118619 A, May 11, 1989, abstract.

* cited by examiner

Primary Examiner—Elizabeth M. Cole
(74) Attorney, Agent, or Firm—Dority & Manning, P.A.

(57) ABSTRACT

The present invention is directed to crimped and resilient polymeric fibers and to fabrics and laminates made from the fibers. In general, the fibers are produced by crimping a polymeric fiber and then cross-linking a polymer and/or monomer contained within the fiber. Cross-linking the polymer makes the crimp contained with the fiber more permanent and more resilient. When formed into a nonwoven web, the fibers produce high loft fabrics which are resilient to compressive forces. Nonwoven webs made in accordance with the present invention are particularly well suited for use in filter products and liquid absorbent products.

38 Claims, 2 Drawing Sheets

CRIMPED POLYMERIC FIBERS AND NONWOVEN WEBS MADE THEREFROM WITH IMPROVED RESILIENCY

FIELD OF THE INVENTION

The present invention is generally directed to crimped polymeric fibers and to nonwoven webs and laminates made from the fibers. More particularly, the present invention is directed to making crimped fibers more resilient to external forces, such as compressive forces, so that nonwoven webs made from the fibers retain their high loft characteristics.

BACKGROUND OF THE INVENTION

High loft, low density webs and fabrics are used for a variety of technical applications. Filtration media utilize high loft fabrics where the density of the fabric (weight/unit volume) and the fiber sizes determine pore size, fiber surface area, and pressure drop through the fabric. These properties determine the functionality, efficiency and capacity of the filter.

These same properties of fiber size, density and loft or bulk affect fluid distribution and the capacity of high loft fabrics designed to hold, transport and distribute fluids in absorbent articles. For instance, such high loft and low density fabrics, particularly nonwoven webs, are used in such products such as towels, industrial wipers, incontinence products, infant care products such as baby diapers, absorbent feminine care products, professional health care articles, and loop materials for hook and loop fasteners, such as VELCRO fasteners.

Some of these products are often made with multiple layers of nonwoven fabrics to obtain a desired combination of properties such as softness, strength, uniformity, and liquid handling properties. For example, disposable baby diapers made from polymeric nonwoven fabrics may include a soft and porous liner layer which fits next to the baby's skin, an impervious outer cover layer which is strong and soft, and one or more interior liquid handling layers which should be soft, absorbent, and have a very high loft.

Unfortunately, although methods exist for producing high loft and low density fabrics, the fabrics are typically subjected to a number of processes during conversion which compress the material and reduce the overall bulk that was created.

Compression can result from winding the fabrics during fabric manufacturing, winding of composites produced utilizing the high loft fabrics, fabrication steps where compression is necessary for adhesion, registration, etc., packaging where compression is used to minimize unit volumes for shipping and during use of the fabric. All of these steps reduce loft and bulk of the high loft fabrics. When the articles are unpacked for application or use or during use, the high loft webs need to recover their loft to the necessary fabric density to insure proper function. Fabrics which do not recover have poor performance and can result in product failures.

Filters will develop excessive pressure drop and will not perform as designed if the high loft structure does not recover. Absorbent articles, on the other hand, have reduced ability to hold and distribute fluids effectively which results in increased leakage.

Thus, a need currently exists for a process for producing high loft fabrics that are resilient to compressive forces. More specifically, high loft fabrics are typically made from crimped polymeric fibers. Thus, a need also exists for a process for producing crimped fibers that "bounce back" when compressed. A need further exists for a process for making webs that retain their high loft and low density characteristics.

SUMMARY OF THE INVENTION

The present invention recognizes and addresses the foregoing problems and others experienced in the prior art.

Accordingly, an object of the present invention is to provide improved crimped fibers and nonwoven fabrics made from the fibers.

Another object of the present invention is to provide a process for producing fibers having a resilient crimp.

A further object of the present invention is to provide a process for producing high loft nonwoven webs and laminates that are resilient to compressive forces.

Another object of the present invention is to provide a process for producing crimped polymeric fibers wherein a polymer and/or a monomer incorporated into the fibers is cross-linked after the fibers have been crimped.

Still another object of the present invention is to provide a process for producing resilient crimped fibers that contain a cross-linked polyethylene polymer.

These and other objects of the present invention are achieved by providing a process for producing resilient crimped fibers. In one embodiment, the process is directed to forming crimped fibers containing polyethylene. For example, the fiber can be a monocomponent fiber containing polyethylene or can be a multicomponent fiber having polyethylene as one of the components. For instance, in one embodiment, the crimped fiber can be a bicomponent fiber having a polyethylene component and a polypropylene component. Alternatively, the fiber can be made from a polymer blend containing polyethylene.

According to the present invention, once the fiber is crimped, the polyethylene contained within the fiber is cross-linked. It has been discovered by the present inventors that cross-linking the polyethylene makes the crimp contained within the fibers more permanent and more resilient to compressive forces. After cross-linking, the fibers exhibit a "bounce back" property in that they retake their original shape if compressed or otherwise compacted.

According to the present invention, there are various methods available in order to cross-link the polyethylene contained within the fiber. For instance, the polyethylene can be cross-linked by exposing the fiber to electron beam irradiation. In an alternative embodiment, a cross-linking agent can be combined with the polyethylene which initiates cross-linking during or after the fiber has been formed and crimped. For example, in one embodiment, the cross-linking agent can be a peroxide which causes polyethylene to cross-link when exposed to heat.

In an alternative embodiment, a silane can be used as a cross-linking agent. In particular, silane can be used as a cross linking agent when combined with a peroxide and a catalyst, such as a tin catalyst. Specifically, silane and a peroxide can be blended with a polymer, such as polyethylene, and can cause the polymer to cross link when the polymer is exposed to moisture.

In a further alternative embodiment, the cross-linking agent can be a photoinitiator, which initiates cross-linking of the polyethylene when subjected to electromagnetic radiation, such as ultraviolet radiation. Examples of photoinitiators include benzoins, benzoin ethers, benzophenones, acetophenones, thioxanones, aryladiazonium salts, and mixtures thereof.

Besides using a photoinitiator or in addition to using a photoinitiator, the polymeric fiber of the present invention can contain a monomer, such as a light reactive thermoset monomer. According to the present invention, the thermoset monomer can polymerize when exposed to light energy and provide rigidity to the fiber and/or can cause a polymer contained within the fiber to cross-link. For instance, in one embodiment, triallylcyanurate can be incorporated into a thermoplastic polymer, such as polyethylene, in an amount of at least about 0.25% by weight and particularly from about 0.25% to about 30% by weight.

Various crimped fibers may be used in the present invention including carded fibers, spunbond fibers, and meltblown fibers. The fibers can be crimped mechanically after fiber formation or naturally crimped during fiber formation. As used herein, a naturally crimped fiber is a fiber that is crimped by activating a latent crimp contained in the fiber.

Besides fibers, the present invention is also directed to nonwoven webs made from fibers having a resilient crimp. For instance, in one embodiment, the present invention is directed to making nonwoven webs out of crimped, bicomponent fibers. The fibers can be made according to a melt spinning process, such as a meltblown process or a spunbond process. In this embodiment, the process of the present invention includes the steps of meltspinning multicomponent fibers. The fibers contain a first polymeric component and a second polymeric component. According to the present invention, the first polymeric component may contain a cross-linking agent, such as a photoinitiator.

Once meltspun, the multicomponent fibers are crimped and formed into a nonwoven web. The nonwoven web is then cross-linked. One method is to expose the web to electromagnetic radiation, such as ultraviolet light, which activates a photoinitiator and/or a monomer for causing the first polymeric component to cross-link and thereby make the crimp contained within the fibers more resilient.

Besides using a photoinitiator, the first polymeric component can be cross-linked by using a peroxide or by using a silane and peroxide additive that cause cross-linking when exposed to a tin catalyst and water. In a further alternative embodiment, the first polymeric component can be cross-linked by being exposed to electron beam radiation.

In one embodiment, the first polymeric component is polyethylene, while the second polymeric component is polypropylene. The fibers can be made into continuous filaments.

Besides being directed to fibers and nonwoven webs, the present invention is also directed to laminates incorporating nonwoven webs made according to the present invention. For instance, a laminate can be constructed containing a first nonwoven web adhered to a second nonwoven web. The first nonwoven web can be a high loft, low density web containing cross-linked and crimped polymeric fibers made in accordance with the present invention.

For example, in one embodiment, a laminate can be constructed containing a nonwoven web made in accordance with the present invention attached to a spunbond web or a carded web made from, for instance, polypropylene fibers. This laminate can be used, for instance, as a liner and surge layer incorporated into a liquid absorbent article, such as a diaper. Alternatively, fabrics made in accordance with the present invention can be incorporated into multilayer filtration media.

Other objects, features and aspects of the present invention are discussed in greater detail below.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which.

Figure 1:
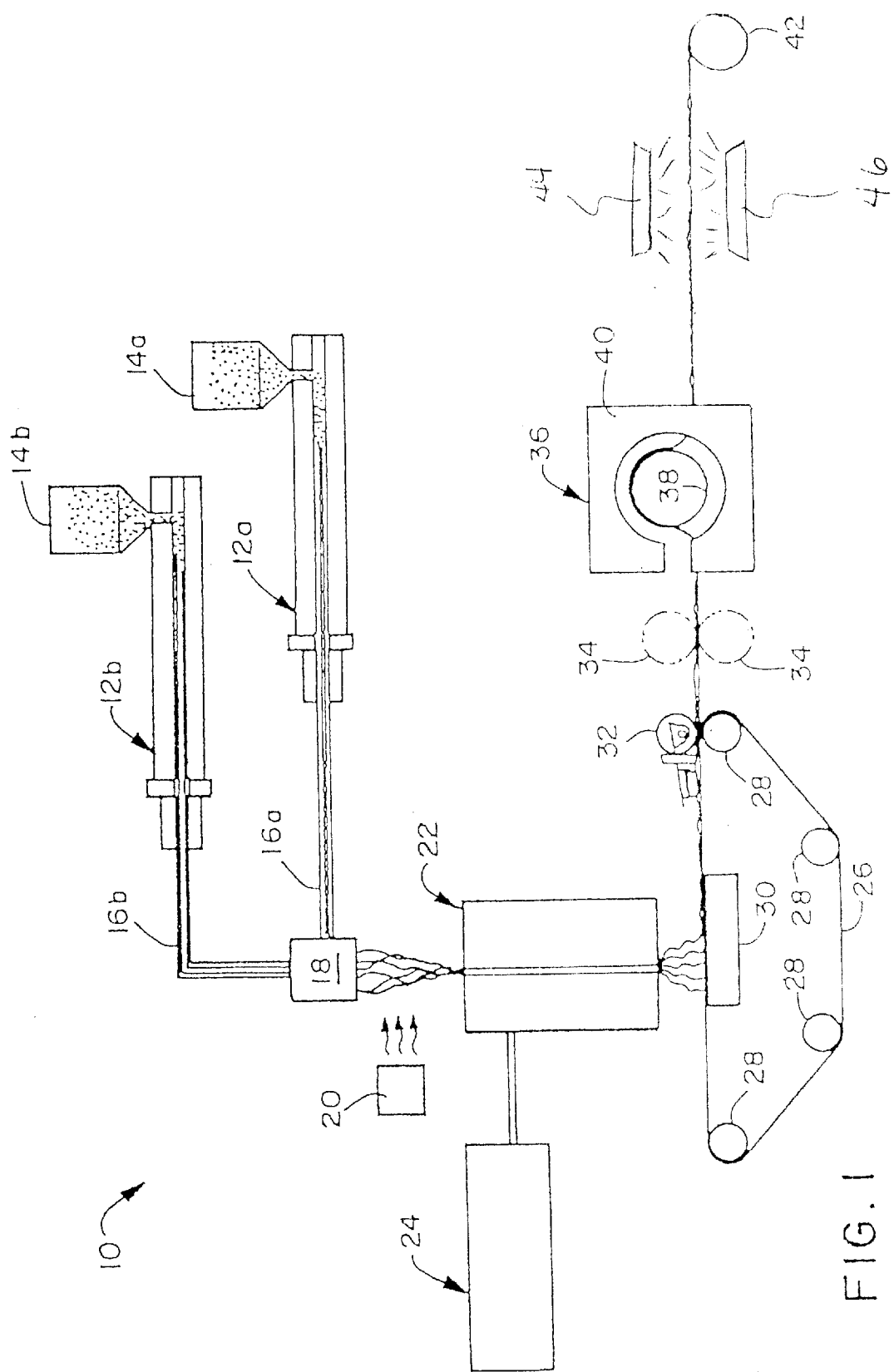
FIG. 1 is a schematic drawing of one embodiment of a process line for making nonwoven webs in accordance with the present invention.

Repeat use of reference characters in the present specification and drawings is intended to represent same or analogous features or elements of the invention.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary construction.

The present invention is generally directed to a process for producing crimped polymeric fibers and to fabrics and laminates made from the fibers. According to the present invention, the fibers are crimped into, for instance, a helical arrangement. Crimping the fibers can increase the bulk, the loftness, the softness, and the drapability of nonwoven webs made from the fibers. Further, crimped fibers can improve the fluid management properties of webs made from the fibers.

More particularly, the present invention is directed to polymeric fibers having a permanent crimp that is resilient to compressive forces. Fibers made according to the present invention will substantially bounce back into their original shape after being compacted.

As described above, one problem that is experienced in the manufacture of high loft, nonwoven webs is that the webs are typically compressed after being formed which can substantially decrease the loft and increase the density of the webs. For instance, the webs can be compressed when the fibers are bonded together or when the webs are laminated to other nonwoven webs. Also, products containing high loft webs are typically packaged very tightly. Unfortunately, compacting the webs can reduce the overall bulk and loft that was initially created.

The present invention, on the other hand, is directed to producing crimped fibers that are resilient to compressive forces. Nonwoven webs made with crimped fibers according to the present invention will recover a substantial amount of loft even if the web is severely compressed during converting and packaging. As such, crimped fibers made according to the present invention offer many advantages and can be used in many different applications, especially in applications where high loft fabrics are desired.

For example, nonwoven webs made in accordance with the present invention are particularly well suited for use as filter media. Since webs made according to the present invention have improved loft characteristics, when used as filter media, the webs exhibit a low pressure drop.

Webs made according to the present invention are also well suited for use as a surge material or in liquid absorbent products since the webs exhibit improved fluid management properties. For example, webs made according to the present invention can be used as a filler material in diapers, in personal care articles, in professional health care articles, and can even be used as loop material for hook and loop fasteners, such as VELCRO fasteners.

In general, fibers made according to the present invention are produced by taking crimped polymeric fibers and cross-linking a polymer contained within the fibers. It has been discovered by the present inventors that by cross-linking a polymer contained within the fibers and/or by incorporating a thermoset polymer into the fibers, the crimp present in the fibers becomes permanent and more resilient to compressive forces. Cross-linking the polymer and/or polymerizing a thermoset monomer in the fibers gives the polymer a set molecular structure that allows webs incorporating the fibers to recover and retain more loft even when compacted. The crimp contained within the fibers is given an inherent memory that causes the crimp to "bounce back" when subjected to external forces. Further, although cross-linking a polymer and/or polymerizing a thermoset monomer contained within the fibers will make the fibers somewhat more rigid, it has been discovered that the fibers will not significantly alter other fabric properties.

In general, any type of crimped, polymeric fiber may be cross-linked in accordance with the present invention. For instance, the fibers can be spunbond fibers, meltblown fibers, or staple fibers. The fibers can be naturally crimped or mechanically crimped. The fibers can be made from a single polymeric material, or can be multicomponent fibers, such as bicomponent fibers. For instance, in one embodiment, the fibers can be bicomponent continuous filaments.

The polymeric material contained within the fibers that is cross-linked will generally depend upon the particular application. For most applications, however, preferably polyethylene is present in the fiber and cross-linked. Further, preferably cross-linking occurs after the fibers have been crimped and after the fibers have been formed into a web. Cross-linking a polymer contained within the fibers prior to formation of the web may interfere with the ability to thermally bond the web together and with the ability to spin the fibers.

Cross-linking a polymer contained within the crimped fibers of the present invention can be accomplished according to various methods. For instance, in one embodiment, the crimped fibers can be exposed to electron beam irradiation which causes a polymer contained within the fibers to cross-link. Electron beam irradiation bombards the polymer chains, such as polyethylene chains, with high energy radiation, which can rip hydrogen atoms from the chains. The process creates radical sites causing the polymer to cross-link.

In an alternative embodiment, a cross-linking agent can be added to the polymer prior to formation of the fiber. For instance, in one embodiment, a peroxide is added to a polymer, such as polyethylene. Peroxide addition can cause cross-linking of polyethylene during melting, extrusion, and spinning processes. For example, heat in an extruder can be used to create free radical sources via the peroxide. The free radicals transfer to the polyethylene initiating the cross-linking reaction. The degree of cross-linking is controlled by the amount of peroxide that is added to the polymer.

In an alternative embodiment, silane in combination with other components can be added to polyethylene in order to cause cross-linking. For instance, in one embodiment, a silane blend containing a peroxide and a tin catalyst, such as di-butyl tin dilaurate, can be meltblended with the polymer, such as polyethylene, that is used to form the fibers. During meltblending, the peroxide is thermally degraded to form free radicals. The peroxide transfers the free radicals to the polymer chain. Before two polymer chains are allowed to cross-link and form a bond to one another, however, the silane molecules "quench" those radical sites and stop the reaction. Each reacted polymer chain is left with a silane molecule grafted to it.

In order to complete the cross-linking process, the polymer can then later be contacted with moisture. The addition of moisture in the presence of the tin catalyst incites two silane molecules, presently grafted to separate polymer chains, to bond to each other. This creates the final cross-linked matrix. Of particular advantage, cross-linking using a silane can be delayed and controlled until after the fibers are formed.

In a preferred embodiment of the present invention, however, cross-linking in the polymer, particularly polyethylene, is accomplished by adding a photoinitiator and/or a thermosetable monomer to the polymer. Once a photoinitiator is added to the polymer, cross-linking of the polymer occurs when the polymer is exposed to electromagnetic radiation, and in particular, ultraviolet radiation. Ultraviolet light at a specific wavelength breaks bonds in the additive creating free radicals which then propagate a cross-linking reaction. Similar to the reaction involving silane, in this embodiment, cross-linking can occur at any point in the process of forming the fiber or forming a nonwoven web incorporating the fiber.

Various photoinitiators can be used according to the process of the present invention. As used herein, a photoinitiator refers to a molecule that absorbs incident light to activate photochemical reactions. More specifically, these molecules form free radicals, or excited donor molecules, to contribute to the polymer chain cross-linking. Preferably, a photoinitiator is chosen that can withstand extrusion temperatures and meltspinning temperatures, without degrading or reacting. Examples of photoinitiators that may be used in the process include free radical photoinitiators, such as benzoins, benzoin ethers, benzophenones, acetophenones, thioxanones, and/or cationic photoinitiators such as aryladiazonium salts. Commercially available photoinitiators include IRGACURE 369 or IRGACURE 907 which are available from the Ciba-Geigy Corporation. The photoinitiators can be added to the polymer alone or in combination. In one embodiment, one or more photoinitiators can be added to polyethylene in an amount up to 10% by weight, particularly in an amount from about 0.25% to about 5% by weight, and more particularly in an amount from about 0.25% to about 2% by weight.

Besides using a photoinitiator or in addition to using a photoinitiator, a thermoset monomer can be added to the polymer in order to increase the rigidity of the fiber. More particularly, preferably a thermoset monomer is used that polymerizes when exposed to free radicals such as those initiated by electromagnetic radiation, such as ultraviolet light.

For example, in one embodiment, the thermoset monomer can be triallylcyanurate. When added to a polymer and formed into fibers, triallylcyanurate monomer can later be polymerized by being exposed to radicals initiated by ultraviolet light. In accordance with the present invention, the triallylcyanurate monomer can be added to the polymer either alone or in combination with photoinitiators. When exposed to radicals initiated by ultraviolet light, it is believed that triallylcyanurate polymerizes into a thermoset polymer and/or causes the polymer used to form the fiber to cross-link.

When present, the thermoset monomer can be added to the polymer in an amount up to about 30% by weight, particularly in an amount up to about 10% by weight, and more particularly in an amount from about 0.25% to about 5% by weight.

One preferred embodiment of the present invention will now be discussed in detail with respect to the accompanying figures. The following process is directed to cross-linking bicomponent, component and a polypropylene component. It should be understood, however, that the following description is for exemplary purposes only and it should be understood that other types of fibers and polymers may be used in accordance with the present invention.

Multicomponent filaments for use in the present invention contain at least two polymeric components. The polymeric components can be, for instance, in a side-by-side configuration or in an eccentric sheath-core configuration. The polymeric components can be selected from semi-crystalline and crystalline thermoplastic polymers which when spun together develop latent crimp.

It is believed that the latent crimpability of multicomponent filaments is created in the filaments due to the differences in the shrinkage properties between the polymeric components. Accordingly, the resulting filaments possess latent crimpability, and such latent crimpability can be activated by subjecting the filaments to heat sufficient to activate crimping.

In one embodiment of the present invention, a polymeric fabric is made from continuous bicomponent filaments comprising a first polymeric component A and a second polymeric component B. The bicomponent filaments have a cross-section, a length, and a peripheral surface. The first and second components A and B are arranged in substantially distinct zones across the cross-section of the bicomponent filaments and extend continuously along the length of the bicomponents filaments. The second component B constitutes at least a portion of the peripheral surface of the bicomponent filaments continuously along the length of the bicomponent filaments.

Figure 2A:
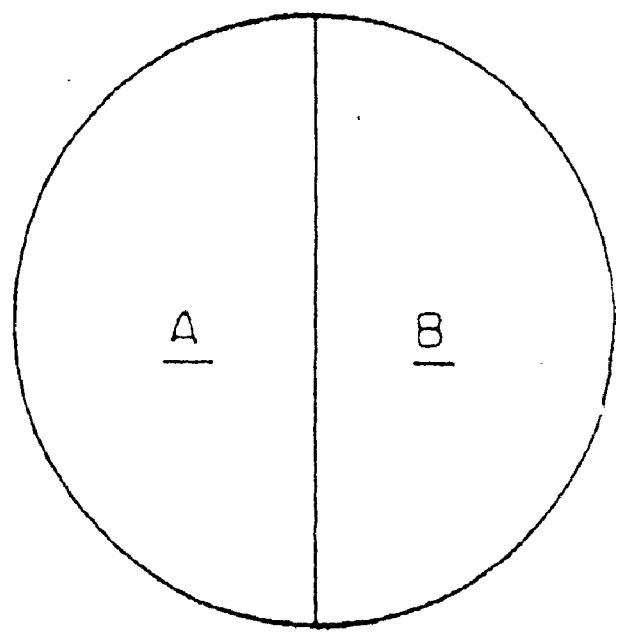
FIG. 2A is a schematic drawing illustrating the cross section of a fiber made according to an embodiment of the present invention with the polymer components A and B in a side-by-side arrangement.
Figure 2B:
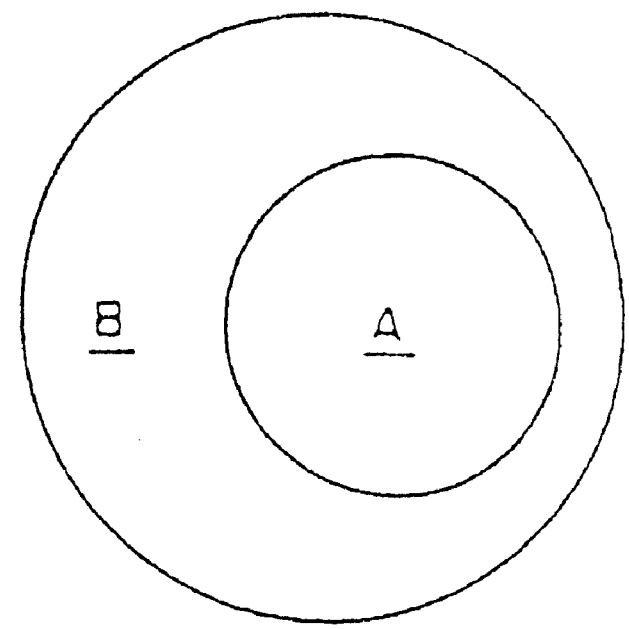
FIG. 2B is a schematic drawing illustrating the cross section of a fiber made according to an embodiment of the present invention with the polymer components A and B in an eccentric sheath/core arrangement.

The first and second components A and B are arranged in either a side-by-side arrangement as shown in FIG. 2A or an eccentric sheath/core arrangement as shown in FIG. 2B if the filaments are to exhibit a natural helical crimp. Polymer component A is the core of the filament and polymer component B is the sheath in the sheath/core arrangement. Methods for extruding multicomponent polymeric filaments into such arrangements are well-known to those of ordinary skill in the art.

In one embodiment, polymer component A can comprise polypropylene or a random copolymer containing polypropylene, such as a copolymer of propylene and butylene.

Polymer component B, on the other hand, preferably comprises polyethylene such as linear low density polyethylene or high density polyethylene, or a random copolymer of propylene and ethylene. As described above, for most applications, polyethylene will be cross-linked according to the present invention after the fiber has been crimped.

Suitable materials for preparing the multicomponent filaments of the present invention include ESCORENE 3445 polypropylene available from Exxon of Houston, Tex., random copolymer of propylene and ethylene available from Union Carbide as grade No. 6D43, ASPUN 6811A linear low density polyethylene available from the Dow Chemical Company of Midland, Mich., and 25355 high density polyethylene available from the Dow Chemical Company.

When polypropylene is component A and polyethylene is component B, the bicomponent filaments may comprise from about 20 to about 80% by weight component A and from about 20 to about 80% component B. More preferably, the filaments comprise from about 40 to about 60% by weight component A and from about 40 to about 60% by weight component B.

In accordance with one embodiment of the present invention, a primary cross-linking agent, such as a photoinitiator, and/or secondary cross-linking agent, such as a monomer, is combined with polymer component B prior to formation of the filaments. For instance, the polymer and the cross-linking agent can be blended and extruded together during formation of the filament. Alternatively, the cross-linking agent and polymer component can be melt blended prior to being formed into the filaments of the present invention. For instance, the polymer component and cross-linking agent can be extruded through a twin screw extruder and formed into pellets prior to being melt spun into filaments.

One process for producing multicomponent filaments and nonwoven webs according to the present invention will now be discussed in detail with reference to FIG. 1. The following process is similar to the process described in U.S. Pat. No. 5,382,400 to Pike et al., which is incorporated herein by reference in its entirety.

Turning to FIG. 1, a process line 10 for preparing one embodiment of the present invention is disclosed. The process line 10 is arranged to produce bicomponent continuous filaments, but it should be understood that the present invention comprehends nonwoven fabrics made with multicomponent filaments having more than two components. For example, the fabric of the present invention can be made with filaments having three or four components.

The process line 10 includes a pair of extruders 12a and 12b for separately extruding a polymer component A and a polymer component B. Polymer component A is fed into the respective extruder 12a from a first hopper 14a and polymer component B is fed into the respective extruder 12b from a second hopper 14b. Polymer components A and B are fed from the extruders 12a and 12b thrgough respective polymer conduits 16a and 16b to a spinneret 18.

Spinnerets for extruding bicomponent filaments are well-known to those of ordinary skill in the art and thus are not described here in detail. Generally described, the spinneret 18 includes a housing containing a spin pack which includes a plurality of plates stacked one on top of the other with a pattern of openings arranged to create flow paths for directing polymer components A and B separately through the spinneret. The spinneret 18 has openings arranged in one or more rows. The spinneret openings form a downwardly extending curtain of filaments when the polymers are extruded through the spinneret. Spinneret 18 may be arranged to form side-by-side or eccentric sheath/core bicomponent filaments illustrated in FIGS. 2A and 2B.

The process line 10 also includes a quench blower 20 positioned adjacent the curtain of filaments extending from the spinneret 18. Air from the quench air blower 20 quenches the filaments extending from the spinneret 18. The quench air can be directed from one side of the filament curtain as shown FIG. 1, or both sides of the filament curtain.

A fiber draw unit or aspirator 22 is positioned below the spinneret 18 and receives the quenched filaments. Fiber draw units or aspirators for use in melt spinning polymers are well-known as discussed above. Suitable fiber draw units for use in the process of the present invention include a linear fiber aspirator of the type shown in U.S. Pat. No. 3,802,817 and eductive guns of the type shown in U.S. Pat. Nos. 3,692,618 and 3,423,266, the disclosures of which are incorporated herein by reference.

Generally described, the fiber draw unit 22 includes an elongate vertical passage through which the filaments are drawn by aspirating air entering from the sides of the passage and flowing downwardly through the passage. A heater or blower 24 supplies aspirating air to the fiber draw unit 22. The aspirating air draws the filaments and ambient air through the fiber draw unit.

An endless foraminous forming surface 26 is positioned below the fiber draw unit 22 and receives the continuous filaments from the outlet opening of the fiber draw unit. The forming surface 26 travels around guide rollers 28. A vacuum 30 positioned below the forming surface 26 where the filaments are deposited draws the filaments against the forming surface.

The process line 10 further includes a bonding apparatus such as thermal point bonding rollers 34 (shown in phantom) or a through-air bonder 36. Thermal point bonders and through-air bonders are well-known to those skilled in the art and are not described here in detail. Generally described, the through-air bonder 36 includes a perforated roller 38, which receives the web, and a hood 40 surrounding the perforated roller. Lastly, the process line 10 includes a winding roll 42 for taking up the finished fabric.

To operate the process line 10, the hoppers 14a and 14b are filled with the respective polymer components A and B. Polymer components A and B are melted and extruded by the respective extruders 12a and 12b through polymer conduits 16a and 16b and the spinneret 18. In accordance with the present invention, polymer component B can contain a cross-linking agent such as a photoinitiator for later cross-linking the polymer. As described above, the photoinitiator can be blended with the polymer as it is fed through extruder 12b or the polymer can be premixed with the additive. Although the temperatures of the molten polymers vary depending on the polymers used, when polypropylene or polyethylene are used as the components, the preferred temperatures of the polymers when extruded range from about 370° to about 530° F. and preferably range from 400° to about 450° F.

As the extruded filaments extend below the spinneret 18, a stream of air from the quench blower 20 at least partially quenches the filaments.

After quenching, the filaments are drawn into the vertical passage of the fiber draw unit 22 by a flow of a gas, such as air, from the heater or blower 24 through the fiber draw unit. The flow of gas causes the filaments to draw or attenuate which develops a latent helical crimp in the filaments. The fiber draw unit is preferably positioned 30 to 60 inches below the bottom of the spinneret 18. Upon exiting, the fibers are crimped although some crimping may occur in the fiber draw unit.

The filaments are deposited through the outlet opening of the fiber draw unit 22 onto the traveling forming surface 26. The vacuum 30 draws the filaments against the forming surface 26 to form an unbonded, nonwoven web of continuous filaments. If necessary, the web is then lightly compressed by a compression roller 32 and then thermal point bonded by rollers 34 or through-air bonded in the through-air bonder 36.

In the through-air bonder 36 as shown in FIG. 1, air having a temperature above the melting temperature of component B and equal to or below the melting temperature of component A is directed from the hood 40, through the web, and into the perforated roller 38. The hot air melts the polymer component B and thereby forms bonds between the bicomponent filaments to integrate the web. When polypropylene and polyethylene are used as polymer components, the air flowing through the through-air bonder preferably has a temperature ranging from about 230° to about 280° F. and a velocity from about 100 to about 500 feet per minute. The dwell time of the web in the through-air bonder is preferably less than about 6 seconds. It should be understood, however, that the parameters of the through-air bonder depend on factors such as the type of polymers used and thickness of the web.

When through-air bonded, the fabric of the present invention characteristically has a relatively high loft. The helical crimp of the filaments creates an open web structure with substantial void portions between filaments and the filaments are bonded at points of contact. The through-air bonded web of the present invention typically has a density of from about 0.015 g/cc to about 0.065 g/cc and a basis weight of from about 0.25 to about 6 oz. per square yard and more preferably from about 1.0 to about 3.5 oz. per square yard.

After being bonded, in the embodiment illustrated in FIG. 1, the web is subjected to ultraviolet radiation using lamps 44 and 46. As shown, preferably the web is exposed to ultraviolet radiation from both sides. Further, if desired, a succession of lamps emitting ultraviolet radiation can be positioned above and below the web. The ultraviolet radiation causes the polyethylene contained in the web to cross-link by activating a photoinitiator. Due to cross-linking, the crimp contained within the fibers becomes more resilient making the web more resilient to compressive forces.

As described above, besides containing a photoinitiator, the polymeric fibers can also contain a thermoset monomer. The thermoset monomer can also be activated by radicals initiated by ultraviolet radiation which causes the monomer to polymerize and/or can also cause cross-linking within the polyethylene.

Lastly, the finished web is wound onto the winding roller 42 and is ready for further treatment or use.

Although the methods of bonding shown in FIG. 1 are thermal point bonding and through-air bonding, it should be understood that the fabric of the present invention may be bonded by other means such as oven bonding, ultrasonic bonding, hydroentangling or combinations thereof. Such bonding techniques are well-known to those of ordinary skill in the art and are not discussed here in detail.

Once produced, the nonwoven webs of the present invention can be used in many different and various applications. For instance, the webs can be used in filter products, in liquid absorbent products, in personal care articles, in garments, and in various other products.

In one embodiment, the nonwoven webs of the present invention can be combined with other nonwoven webs to form a laminate. For instance, a nonwoven web made in accordance with the present invention can be used as a surge layer and combined with a liner layer for use in diapers and other similar products. Alternatively, webs made in accordance with the present invention can be incorporated into multi-layer filter products.

A multi-layer laminate may be formed by a number of different techniques including, but not limited to, using adhesives, needle punching, ultrasonic bonding, thermal calendering and any other method known in the art.

The present invention may be better understood with reference to the following example.

EXAMPLE

The following tests were conducted in order to demonstrate the resiliency of nonwoven fabrics made in accordance with the present invention.

Weighted Percent Recovery

The Weighted Percent Recovery measures the normalized percent bulk recovered by a fabric after being compressed for a standardized period of time. The fabric test sample is prepared by cutting 2.25" diameter fabric layers and stacking them to a total height of 20 mm. This stack is defined as the sample plug. The weight, exact height, and number of layers in the pre-compressed sample plug are recorded. Note: Recorded thickness is the first value measured that is held for 3 seconds without dropping on the Starrett Bulk tester (exerts 0.013 PSI on the sample). The sample is then placed in a 2.25 diameter Carver Test Cylinder (#2091.2) and compressed in the Carver Press Apparatus (#2031) to a pressure of 1,500 PSI for a period of 60 seconds. After relieving the pressure and removing the sample plug from the test cylinder, the compressed plug stack height is immediately measured. The stack height is subsequently measured and recorded every 60 seconds for 4 minutes. Data is then plotted as "weighted percent recovery vs. time" where:

$$Weighted\ \%\ Recovery = \frac{StackHt\ t}{StackHt\ i} * \frac{Target20mmPlugWt}{ActualPlugWt}$$

Stack Ht(t) Stack height measured at time t after compression (mm)

Stack Ht(i) Stack height measured before compression (mm)

Actual Plug Wt. The weight of the plug before compression (g)

Target 20 mm Wt. Target weight of stack to normalize data (g)

For the following examples, data has been averaged over 3 individual samples.

Examples 1–6 (E1–E6)

Approximately 3.0 ounce per square yard (osy) spunbond nonwoven webs were prepared from side-by-side bicomponent fibers of linear low density polyethylene (LLDPE) and polypropylene (PP) using the bicomponent conjugate fiber production process disclosed in U.S. Pat. No. 5,382,400. Drawing air was heated and supplied at 177° C. to the draw unit for fiber attenuation. LLDPE, Aspun 6811A, which is available from Dow Chemical, was blended with various levels (0–1%) of photoinitiator and/or monomer, as described in Table 1 below. The photoinitiators used were Ciba-Giegy IRGACURE 369 and IRGACURE 907, and the monomer used was Tri Allyl Cyanurate (TAC) which were compounded into low density polyethylene pellets. This mixture was fed into a first single screw extruder. Polypropylene, Exxon 3445, was blended with 2% weight of a $TiO_2$ concentrate containing 50% by weight of $TiO_2$ and 50% by weight of polypropylene. This mixture was then fed into a second single screw extruder. The extruded polymers were spun into bicomponent fibers using a side-by-side bicomponent spinning die which had a 0.6 mm spinhole diameter and 6:1 L/D ratio. The ratio of the two polymer extrudates fed through the die to form the fibers was controlled at 50% LLDPE blend/50% polypropylene blend. The temperature of the molten polymers being fed into the die was kept at 232° C., and the spinhole throughput was 0.7 grams/hole/minute. The fibers were quenched using quench air at 18° C. The quenched fibers were drawn in an aspirating unit of the type which is described in U.S. Pat. No. 3,802,817 to Matuski et al. The weight-per-unit-length measurement of the drawn fibers was about 3.0–3.5 denier per filament. The drawn fibers were then deposited on a foraminous forming surface with the assist of a vacuum flow to form an unbonded fiber web.

The unbonded fiber web was bonded by passing the web through a hot air bonding unit, using 121–140° C. air to bond the fibers to one another.

Samples were then irradiated with ultraviolet light. The equipment used to irradiate the samples was similar to the systems disclosed in U.S. Pat. Nos. 3,911,318; 3,872,349; 3,983,039; 4,042,850; 4,208,587; 4,359,668; 4,313,969; 4,269,581; 4,485,332; 4,507,587 which are all incorporated herein by reference. Samples cut into single layers of 12"×14" fabric were exposed on each side to UV light at 600W/in$^2$ at line speeds 50, 100, or 200 fpm, as shown in Table 1. The two ultraviolet light spectra used to irradiate the samples were either the D-Bulb or H-Bulb spectra. Irradiation was performed in a non-nitrogenated environment, at standard atmospheric temperature, pressure, and humidity.

Comparative Examples 1–3 (C1–C3)

Fabrics were spun and bonded in accordance with the procedure described in Example 1. These comparative samples do contain additives, however, they were not exposed to any form of UV irradiation.

Examples 7–8 (E7–E8)

Fabrics were spun and irradiated in accordance with the procedures described in Example 1. However, these samples were bonded by passing the web through a nip formed by two pattern rolls. The pattern rolls were steel rolls which have different patterned configurations of regularly spaced raised points (bonding points) on the surfaces and were equipped with heating means. Both of the bonding rolls had a diameter of about 61 cm. The bonding pin pressure was applied by the bonding rolls on the web, and the rolls were heated to a temperature capable of melting and binding the fibers. The fabrics were then irradiated.

Comparative Examples 4–5 (C4–C5)

Fabrics were spun in accordance with the method described in Example 1. Fabrics were then bonded in accordance with the point bonding method described in Example 7. However, these comparative samples were not exposed to any form of UV irradiation or electron beam.

Examples 9–11 (E9–E11)

Fibrous structures were spun and bonded in accordance with the methods described in Example 1. However, these fabrics were not irradiated with UV light. Instead, they were exposed to electron beam irradiation at levels between 5 and 10 MRad. Samples were prepared for exposure by cutting fabrics into 30"×14" sheets and running the samples through electron beam exposure on a moving cart, layered 10 sheets thick. Irradiation was performed in a non-nitrogenated environment at standard atmospheric temperature, pressure, and humidity.

Comparative Example 6 (C6)

Fabrics were spun and bonded in accordance with the method described in Example 1. However, these comparative samples were not exposed to any form of UV irradiation or electron beam.

TABLE 1

|     | Basis Wt (OSY) | PE Additive A | PE Additive B | Bonding Method | UV Bulb | UV Line Speed (fpm) | E Beam Dosage (MRad) | Weighted % Recov. at 4 min |
|-----|------|-----------|------------|---------|-----|------|-----|------|
| E1  | 3.0  | 0.5% 369  | 0.25% TAC  | TAB     | D   | 50   | —   | 80.9 |
| E2  | 3.0  | 0.5% 907  | 0.25% TAC  | TAB     | D   | 50   | —   | 58.5 |
| C1  | 3.0  | 0.5% 369  | 0.25% TAC  | TAB     | Not | Treated | — | 55.8 |
| C2  | 3.0  | 0.5% 907  | 0.25% TAC  | TAB     | Not | Treated | — | 53.7 |
| E3  | 3.0  | 0.75% 369 | 0.25% TAC  | TAB     | D   | 100  | —   | 68.0 |
| E4  | 3.0  | 0.75% 369 | 0.25% TAC  | TAB     | D   | 50   | —   | 68.1 |
| E5  | 3.0  | 0.75% 369 | 0.25% TAC  | TAB     | H   | 100  | —   | 62.0 |
| E6  | 3.0  | 0.75% 369 | 0.25% TAC  | TAB     | H   | 50   | —   | 60.6 |
| C3  | 3.0  | 0.75% 369 | 0.25% TAC  | TAB     | Not | Treated | — | 54.1 |
| E7  | 3.0  | —         | 1% TAC     | Pattern | D   | 50   | —   | 85.9 |
| E8  | 3.0  | —         | 1% TAC     | Pattern | H   | 50   | —   | 83.9 |
| C4  | 3.0  | —         | 1% TAC     | Pattern | Not | Treated | — | 65.9 |
| C5  | 3.0  | —         | —          | Pattern | Not | Treated | — | 57.4 |
| E9  | 3.0  | —         | —          | TAB     | —   | —    | 5   | 71.9 |
| E10 | 3.0  | —         | —          | TAB     | —   | —    | 7.5 | 90.4 |
| E11 | 3.0  | —         | —          | TAB     | —   | —    | 10  | 82.8 |
| C6  | 3.0  | —         | —          | TAB     | —   | —    | Not Treated | 68.7 |

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A process for producing resilient nonwoven webs from crimped fibers comprising the steps of:
   a) Providing a crimped fiber made from a polymeric material, said polymeric material comprising polyethylene;
   b) Forming said crimped fiber into a nonwoven web; and
   c) Thereafter, cross-linking said polyethylene contained in said crimped fiber thereby making the crimp present in said fiber more resilient to compression.

2. A process as defined in claim 1, wherein said crimped fiber comprises a bicomponent fiber.

3. A process as defined in claim 1, wherein said crimped fiber comprises a spunbond fiber.

4. A process as defined in claim 1, wherein said crimped fiber comprises a staple fiber.

5. A process as defined in claim 1, wherein said crimped fiber further contains a photoinitiator combined with said polyethylene and wherein said polyethylene is cross-linked by exposing said fiber to ultraviolet radiation, said ultraviolet radiation activating said photoinitiator for causing said polyethylene to cross-link.

6. A process as defined in claim 1, wherein said crimped fiber further contains a thermoset monomer and wherein said polyethylene is cross-linked by exposing said fiber to ultraviolet radiation, said ultraviolet radiation initiating free radicals causing said monomer to polymerize and to cross-link said polyethylene.

7. A process as defined in claim 6, wherein said thermoset monomer comprises triallylcyanurate.

8. A process as defined in claim 1, wherein said polyethylene is cross-linked by exposing said fiber to electron beam irradiation.

9. A process as defined in claim 1, wherein said crimped fiber further contains a cross-linking agent combined with said polyethylene, said cross-linking agent initiating cross-linking of said polyethylene.

10. A process as defined in claim 9, wherein said cross-linking agent comprises a peroxide.

11. A process as defined in claim 9, wherein said cross-linking agent comprises a silane.

12. A process as defined in claim 1, wherein said crimped fiber comprises a continuous filament.

13. A process for producing resilient nonwoven webs from crimped fibers comprising the steps of:
   a) Melt spinning multicomponent fibers, said fibers containing a first polymeric component and a second polymeric component, said first polymeric component containing a cross-linking agent, said cross-linking agent comprising a photoinitiator;
   b) Crimping said multicomponent fibers;
   c) Forming said multicomponent fibers into a nonwoven web; and
   d) Exposing said nonwoven web to electromagnetic radiation, said electromagnetic radiation activating said photoinitiator for causing said first polymeric component to cross-link.

14. A process as defined in claim 13, wherein said first polymeric component comprises polyethylene.

15. A process as defined in claim 14, wherein said electromagnetic radiation comprises ultraviolet light.

16. A process as defined in claim 15, wherein said second polymeric component comprises polypropylene.

17. A process as defined in claim 15, wherein said first polymeric component further contains triallylcyanurate, said triallylcyanurate being present in said first polymeric component in an amount of at least 0.25% by weight, said triallylcyanurate polymerizing when exposed to the electromagnetic radiation.

18. A process as defined in claim 17, wherein said triallylcyanurate is present in said first polymeric component in an amount from about 0.25% to about 2% by weight.

19. A process as defined in claim 15, wherein said multicomponent fibers comprise continuous filaments.

20. A resilient nonwoven web comprising a polymeric fiber having a resilient crimp, said polymeric fiber being made from a polymeric material, said polymeric material comprising polyethylene, said polyethylene being cross-linked after being formed into said nonwoven web thereby making the crimp present in said fiber more resilient to compression.

21. A nonwoven web as defined in claim 20, wherein said fiber comprises a staple fiber.

22. A nonwoven web as defined in claim 20, wherein said fiber comprises a melt extruded filament.

23. A nonwoven web as defined in claim 20, wherein said polyethylene contains a cross-linking agent.

24. A nonwoven web as defined in claim 23, wherein said cross-linking agent comprises a photoinitiator, and wherein said polyethylene has been cross- linked by exposing said polymeric fiber to ultraviolet radiation.

25. A nonwoven web as defined in claim 24, wherein said polymeric fiber comprises a bicomponent fiber having a first polymeric component and a second polymeric component, said first polymeric component comprising polyethylene while said second polymeric component comprising polypropylene.

26. A nonwoven web as defined in claim 23, wherein said cross-linking agent comprises triallylcyanurate.

27. A resilient nonwoven web comprising:
crimped polymeric fibers made from a melt extruded polymeric material, said polymeric material comprising polyethylene, said polyethylene being cross-linked after being formed into said nonwoven web thereby making the crimp present in said fiber more resilient to compressive forces exerted on said nonwoven web.

28. A resilient nonwoven web as defined in claim 27, wherein said fibers contain a cross-linking agent, said cross-linking agent comprising a polymerized thermoset monomer.

29. A resilient nonwoven web as defined in claim 27, wherein said fibers comprise spunbond continuous filaments.

30. A resilient nonwoven web as defined in claim 27, wherein said fibers contain a cross-linking agent.

31. A resilient nonwoven web as defined in claim 30, wherein said cross-linking agent comprises a photoinitiator, and wherein said web has been cross-linked by exposing said web to ultraviolet radiation.

32. A resilient nonwoven web as defined in claim 31, wherein said fibers comprise bicomponent fibers having a first polymeric component and a second polymeric component, said first polymeric component comprising polyethylene while said second polymeric component comprising polypropylene.

33. A resilient nonwoven web as defined in claim 28, wherein said thermoset monomer comprises triallylcyanurate.

34. A process for producing resilient nonwoven webs comprising the steps of:
adding a thermoset monomer to a polyolefin;
meltextruding said polyolefin into fibers;
crimping said fibers;
forming said fibers into a nonwoven web; and
exposing said nonwoven web to ultraviolet light, said ultraviolet light initiating free radicals causing said thermoset monomer to polymerize thereby causing the rigidity of said crimped fibers to increase.

35. A process as defined in claim 34, wherein said polyolefin comprises polyethylene.

36. A process as defined in claim 35, wherein said thermoset monomer comprises triallylcyanurate.

37. A process as defined in claim 36, wherein said fibers comprise bicomponent fibers.

38. A process as defined in claim 36, wherein said triallylcyanurate is present within said polyethylene in an amount up to about 10% by weight.

* * * * *